(12) United States Patent
Chermoni

(10) Patent No.: US 8,147,536 B2
(45) Date of Patent: *Apr. 3, 2012

(54) BALLOON CATHETER FOR MULTIPLE ADJUSTABLE STENT DEPLOYMENT

(75) Inventor: Israel S. Chermoni, Haifa (IL)

(73) Assignee: XTENT, Inc., Los Altos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/503,791

(22) Filed: Jul. 15, 2009

(65) Prior Publication Data

US 2009/0299461 A1 Dec. 3, 2009

Related U.S. Application Data

(63) Continuation of application No. 11/625,243, filed on Jan. 19, 2007, now abandoned, which is a continuation of application No. 11/421,653, filed on Jun. 1, 2006, now abandoned, which is a continuation of application No. 10/108,985, filed on Mar. 29, 2002, now Pat. No. 7,147,655.

(30) Foreign Application Priority Data

Mar. 29, 2001 (IL) .......................................... 142332

(51) Int. Cl.
*A61F 2/84* (2006.01)
(52) U.S. Cl. ....................... 623/1.11; 623/903
(58) Field of Classification Search ........ 623/1.11–1.13, 623/1.16, 1.35; 606/108, 194, 198; 604/96.01
See application file for complete search history.

(56) References Cited

U.S. PATENT DOCUMENTS

| 3,173,418 A | 3/1965 | Baran |
| 3,394,075 A | 7/1968 | Smith |
| 3,938,502 A | 2/1976 | Bom |
| 4,292,974 A | 10/1981 | Fogarty et al. |
| 4,323,071 A | 4/1982 | Simpson et al. |
| 4,327,721 A | 5/1982 | Goldin et al. |
| 4,406,656 A | 9/1983 | Hattler et al. |
| 4,417,576 A | 11/1983 | Baran |
| 4,564,014 A | 1/1986 | Fogarty et al. |
| 4,576,177 A | 3/1986 | Webster, Jr. |
| 4,580,568 A | 4/1986 | Gianturco |
| 4,661,094 A | 4/1987 | Simpson |
| 4,665,918 A | 5/1987 | Garza et al. |

(Continued)

FOREIGN PATENT DOCUMENTS

EP 203945 B1 8/1989

(Continued)

OTHER PUBLICATIONS

Born, N. et al."Early and recent intraluminal ultrasound devices," *Internal Journal of Cardiac Imaging*, 1989,4:79-88.

(Continued)

*Primary Examiner* — Elizabeth Houston
(74) *Attorney, Agent, or Firm* — Levine Bagade Han LLP

(57) ABSTRACT

A catheter configured to carry one or more stents and having an inflatable balloon for expanding a stent surrounding the balloon. The catheter is characterized in having a positioner for moving the one or more stents relative to the balloon from a first position in which the stent does not surround the balloon to a second position in which the stent surrounds the balloon. Also disclosed is a method for deploying a stent at a desired location in the vascular system.

31 Claims, 13 Drawing Sheets

U.S. PATENT DOCUMENTS

| | | |
|---|---|---|
| 4,681,110 A | 7/1987 | Wiktor |
| 4,681,564 A | 7/1987 | Landreneau |
| 4,693,243 A | 9/1987 | Buras |
| 4,733,665 A | 3/1988 | Palmaz |
| 4,739,762 A | 4/1988 | Palmaz |
| 4,744,790 A | 5/1988 | Jankowski et al. |
| 4,762,129 A | 8/1988 | Bonzel |
| 4,775,337 A | 10/1988 | Van Wagener et al. |
| 4,775,371 A | 10/1988 | Mueller, Jr. |
| 4,776,337 A | 10/1988 | Palmaz |
| 4,790,315 A | 12/1988 | Mueller |
| 4,790,331 A | 12/1988 | Okada et al. |
| 4,839,623 A | 6/1989 | Schonstedt et al. |
| 4,841,977 A | 6/1989 | Griffith et al. |
| 4,850,358 A | 7/1989 | Millar |
| 4,850,969 A | 7/1989 | Jackson |
| 4,877,030 A | 10/1989 | Beck et al. |
| 4,877,031 A | 10/1989 | Conway et al. |
| 4,886,062 A | 12/1989 | Wiktor |
| 4,892,519 A | 1/1990 | Songer et al. |
| 4,911,163 A | 3/1990 | Fina |
| 4,917,097 A | 4/1990 | Proudian et al. |
| 4,950,227 A | 8/1990 | Savin et al. |
| 4,950,232 A | 8/1990 | Ruzicka et al. |
| 4,976,689 A | 12/1990 | Buchbinder et al. |
| 4,988,356 A | 1/1991 | Crittenden et al. |
| 4,994,033 A | 2/1991 | Shockey et al. |
| 4,994,066 A | 2/1991 | Voss |
| 4,994,069 A | 2/1991 | Ritchart et al. |
| 5,000,734 A | 3/1991 | Boussignac et al. |
| 5,007,897 A | 4/1991 | Kalb et al. |
| 5,009,636 A | 4/1991 | Wortley et al. |
| 5,014,089 A | 5/1991 | Sakashita et al. |
| 5,015,232 A | 5/1991 | Maglinte |
| 5,019,042 A | 5/1991 | Sahota |
| 5,019,090 A | 5/1991 | Pinchuk |
| 5,026,377 A | 6/1991 | Burton et al. |
| 5,034,001 A | 7/1991 | Garrison et al. |
| 5,041,089 A | 8/1991 | Mueller et al. |
| 5,046,497 A | 9/1991 | Millar |
| 5,049,132 A | 9/1991 | Shaffer et al. |
| 5,064,435 A | 11/1991 | Porter |
| 5,087,244 A | 2/1992 | Wolinsky et al. |
| 5,087,247 A | 2/1992 | Horn et al. |
| 5,092,877 A | 3/1992 | Pinchuk |
| 5,102,390 A | 4/1992 | Crittenden et al. |
| 5,102,415 A | 4/1992 | Guenther et al. |
| 5,102,417 A | 4/1992 | Palmaz |
| 5,104,404 A | 4/1992 | Wolff |
| 5,108,416 A | 4/1992 | Ryan et al. |
| 5,112,303 A | 5/1992 | Pudenz et al. |
| 5,112,305 A | 5/1992 | Barath et al. |
| 5,123,917 A | 6/1992 | Lee |
| 5,135,535 A | 8/1992 | Kramer |
| 5,158,548 A | 10/1992 | Lau et al. |
| 5,163,921 A | 11/1992 | Feiring |
| 5,163,952 A | 11/1992 | Froix |
| 5,163,958 A | 11/1992 | Pinchuk |
| 5,180,364 A | 1/1993 | Ginsburg |
| 5,180,366 A | 1/1993 | Woods |
| 5,180,368 A | 1/1993 | Garrison |
| 5,192,307 A | 3/1993 | Wall |
| 5,195,984 A | 3/1993 | Schatz |
| 5,203,338 A | 4/1993 | Jang |
| 5,213,576 A | 5/1993 | Abiuso et al. |
| 5,217,495 A | 6/1993 | Kaplan et al. |
| 5,219,326 A | 6/1993 | Hattler |
| 5,219,335 A | 6/1993 | Willard et al. |
| 5,219,355 A | 6/1993 | Parodi et al. |
| 5,226,888 A | 7/1993 | Arney |
| 5,226,913 A | 7/1993 | Pinchuk |
| 5,242,396 A | 9/1993 | Evard |
| 5,242,399 A | 9/1993 | Lau et al. |
| 5,242,451 A | 9/1993 | Harada et al. |
| 5,246,421 A | 9/1993 | Saab |
| 5,254,089 A | 10/1993 | Wang |
| 5,257,974 A | 11/1993 | Cox |
| 5,261,878 A | 11/1993 | Galindo |
| 5,266,073 A | 11/1993 | Wall |
| 5,273,536 A | 12/1993 | Savas |
| 5,281,200 A | 1/1994 | Corso, Jr. et al. |
| 5,282,785 A | 2/1994 | Shapland et al. |
| 5,284,473 A | 2/1994 | Calabria |
| 5,295,962 A | 3/1994 | Crocker et al. |
| 5,300,085 A | 4/1994 | Yock |
| 5,306,250 A | 4/1994 | March et al. |
| 5,308,356 A | 5/1994 | Blackshear, Jr. et al. |
| 5,318,535 A | 6/1994 | Miraki |
| 5,334,187 A | 8/1994 | Fischell et al. |
| 5,344,401 A | 9/1994 | Radisch et al. |
| 5,344,426 A | 9/1994 | Lau et al. |
| 5,358,487 A | 10/1994 | Miller |
| 5,360,401 A | 11/1994 | Turnland et al. |
| 5,360,443 A | 11/1994 | Barone et al. |
| 5,364,356 A | 11/1994 | Hofling |
| 5,364,928 A | 11/1994 | Ash |
| 5,370,617 A | 12/1994 | Sahota |
| 5,378,237 A | 1/1995 | Boussignac et al. |
| 5,382,261 A | 1/1995 | Palmaz |
| 5,395,333 A | 3/1995 | Brill |
| 5,409,495 A | 4/1995 | Osborn |
| 5,411,507 A | 5/1995 | Heckele |
| 5,415,637 A | 5/1995 | Khosravi |
| 5,421,955 A | 6/1995 | Lau et al. |
| 5,425,709 A | 6/1995 | Gambale |
| 5,433,706 A | 7/1995 | Abiuso |
| 5,439,445 A | 8/1995 | Kontos |
| 5,443,500 A | 8/1995 | Sigwart |
| 5,468,298 A | 11/1995 | Lei et al. |
| 5,478,349 A | 12/1995 | Nicholas |
| 5,501,227 A | 3/1996 | Yock |
| 5,507,768 A | 4/1996 | Lau et al. |
| 5,507,771 A | 4/1996 | Gianturco |
| 5,514,093 A | 5/1996 | Ellis et al. |
| 5,514,154 A | 5/1996 | Lau et al. |
| 5,527,354 A | 6/1996 | Fontaine et al. |
| 5,534,007 A | 7/1996 | St. Germain et al. |
| 5,545,209 A | 8/1996 | Roberts et al. |
| 5,549,551 A | 8/1996 | Peacock, III et al. |
| 5,549,563 A | 8/1996 | Kronner |
| 5,549,635 A | 8/1996 | Solar |
| 5,554,181 A | 9/1996 | Das |
| 5,562,725 A | 10/1996 | Schmitt et al. |
| 5,591,222 A | 1/1997 | Susawa et al. |
| 5,607,463 A | 3/1997 | Schwartz et al. |
| 5,620,457 A | 4/1997 | Pinchasik et al. |
| 5,628,775 A | 5/1997 | Jackson et al. |
| 5,634,928 A | 6/1997 | Fischell et al. |
| 5,662,675 A | 9/1997 | Polanskyj Stockert et al. |
| 5,676,654 A | 10/1997 | Ellis et al. |
| 5,683,451 A | 11/1997 | Lenker et al. |
| 5,697,948 A | 12/1997 | Marin et al. |
| 5,722,669 A | 3/1998 | Shimizu et al. |
| 5,735,869 A | 4/1998 | Fernandez-Aceytuno |
| 5,755,772 A | 5/1998 | Evans et al. |
| 5,755,776 A | 5/1998 | Al-Saadon |
| 5,755,781 A | 5/1998 | Jayaraman |
| 5,769,882 A | 6/1998 | Fogarty et al. |
| 5,772,669 A | 6/1998 | Vrba |
| 5,776,141 A | 7/1998 | Klein et al. |
| 5,807,398 A | 9/1998 | Shaknovich |
| 5,824,040 A | 10/1998 | Cox et al. |
| 5,824,041 A | 10/1998 | Lenker et al. |
| 5,833,694 A | 11/1998 | Poncet |
| 5,836,964 A | 11/1998 | Richter et al. |
| 5,843,092 A | 12/1998 | Heller et al. |
| 5,858,556 A | 1/1999 | Eckert et al. |
| 5,870,381 A | 2/1999 | Kawasaki et al. |
| 5,879,370 A | 3/1999 | Fischell et al. |
| 5,891,190 A | 4/1999 | Boneau |
| 5,895,398 A | 4/1999 | Wensel et al. |
| 5,902,332 A | 5/1999 | Schatz |
| 5,961,536 A | 10/1999 | Mickley et al. |
| 5,976,155 A | 11/1999 | Foreman et al. |
| 5,980,484 A | 11/1999 | Ressemann et al. |
| 5,980,486 A | 11/1999 | Enger |
| 5,980,552 A | 11/1999 | Pinchasik et al. |

| | | | | | | |
|---|---|---|---|---|---|---|
| 5,981,190 | A | 11/1999 | Israel | 2001/0044595 A1 | 11/2001 | Reydel et al. |
| 5,984,957 | A | 11/1999 | Laptewicz, Jr. et al. | 2002/0138132 A1 | 9/2002 | Brown |
| 5,985,398 | A | 11/1999 | Bellegarde | 2002/0151955 A1 | 10/2002 | Tran et al. |
| 6,004,348 | A | 12/1999 | Banas et al. | 2002/0156496 A1 | 10/2002 | Chermoni |
| 6,007,517 | A | 12/1999 | Anderson | 2002/0188343 A1 | 12/2002 | Mathis |
| 6,022,359 | A | 2/2000 | Frantzen | 2002/0188347 A1 | 12/2002 | Mathis |
| 6,027,519 | A | 2/2000 | Stanford | 2002/0193873 A1 | 12/2002 | Brucker et al. |
| 6,033,434 | A | 3/2000 | Borghi | 2003/0045923 A1 | 3/2003 | Bashiri |
| 6,039,721 | A | 3/2000 | Johnson et al. | 2003/0114919 A1 | 6/2003 | McQuiston et al. |
| 6,056,722 | A | 5/2000 | Jayaraman | 2003/0114922 A1 | 6/2003 | Iwasaka et al. |
| 6,056,759 | A | 5/2000 | Fiedler | 2003/0130683 A1 | 7/2003 | Andreas et al. |
| 6,066,155 | A | 5/2000 | Amann et al. | 2003/0135258 A1 | 7/2003 | Andreas et al. |
| 6,068,655 | A | 5/2000 | Seguin et al. | 2003/0139796 A1 | 7/2003 | Sequin et al. |
| 6,090,063 | A | 7/2000 | Makower et al. | 2003/0139797 A1 | 7/2003 | Johnson et al. |
| 6,090,136 | A | 7/2000 | McDonald et al. | 2003/0176909 A1 | 9/2003 | Kusleika |
| 6,106,530 | A | 8/2000 | Harada | 2003/0199821 A1 | 10/2003 | Gerdts et al. |
| RE36,857 | E | 9/2000 | Euteneuer et al. | 2004/0087965 A1 | 5/2004 | Levine et al. |
| 6,123,723 | A | 9/2000 | Konya et al. | 2004/0093061 A1 | 5/2004 | Acosta et al. |
| 6,126,685 | A | 10/2000 | Lenker et al. | 2004/0186551 A1 | 9/2004 | Kao et al. |
| 6,129,756 | A | 10/2000 | Kugler et al. | 2004/0215312 A1 | 10/2004 | Andreas |
| 6,143,016 | A | 11/2000 | Bleam et al. | 2004/0215331 A1 | 10/2004 | Chew et al. |
| 6,165,167 | A | 12/2000 | Delaloye | 2004/0249434 A1 | 12/2004 | Andreas et al. |
| 6,174,327 | B1 | 1/2001 | Mertens et al. | 2004/0249435 A1 | 12/2004 | Andreas et al. |
| 6,179,878 | B1 | 1/2001 | Duerig et al. | 2005/0010276 A1 | 1/2005 | Acosta et al. |
| 6,187,034 | B1 | 2/2001 | Frantzen | 2005/0038505 A1 | 2/2005 | Shulze et al. |
| 6,190,402 | B1 | 2/2001 | Horton et al. | 2005/0049673 A1 | 3/2005 | Andreas et al. |
| 6,196,995 | B1 | 3/2001 | Fagan | 2005/0080474 A1 | 4/2005 | Andreas et al. |
| 6,200,337 | B1 | 3/2001 | Moriuchi et al. | 2005/0085888 A1 | 4/2005 | Andreas et al. |
| 6,224,609 | B1 | 5/2001 | Ressemann et al. | 2005/0149159 A1 | 7/2005 | Andreas et al. |
| 6,241,691 | B1 | 6/2001 | Ferrera et al. | 2005/0222603 A1 | 10/2005 | Andreas et al. |
| 6,251,132 | B1 | 6/2001 | Ravenscroft et al. | 2005/0228477 A1 | 10/2005 | Grainger et al. |
| 6,251,134 | B1 | 6/2001 | Alt et al. | 2005/0288763 A1 | 12/2005 | Andreas et al. |
| 6,254,628 | B1 | 7/2001 | Wallace et al. | 2005/0288764 A1 | 12/2005 | Snow et al. |
| 6,258,117 | B1 | 7/2001 | Camrud et al. | 2005/0288766 A1 | 12/2005 | Plain et al. |
| 6,264,683 | B1 | 7/2001 | Stack et al. | 2006/0069424 A1 | 3/2006 | Acosta et al. |
| 6,273,913 | B1 | 8/2001 | Wright et al. | 2006/0080475 A1 | 4/2006 | Andreas et al. |
| 6,312,458 | B1 | 11/2001 | Golds | 2006/0200223 A1 | 9/2006 | Andreas et al. |
| 6,315,794 | B1 | 11/2001 | Richter | 2006/0206190 A1 | 9/2006 | Chermoni |
| 6,319,277 | B1 | 11/2001 | Rudnick et al. | 2006/0229700 A1 | 10/2006 | Acosta et al. |
| 6,325,823 | B1 | 12/2001 | Horzewski et al. | 2006/0271150 A1 | 11/2006 | Andreas et al. |
| 6,334,866 | B1 | 1/2002 | Wall | 2006/0271151 A1 | 11/2006 | McGarry et al. |
| 6,357,104 | B1 | 3/2002 | Myers | 2006/0282147 A1 | 12/2006 | Andreas |
| 6,375,676 | B1 | 4/2002 | Cox | 2006/0282148 A1 | 12/2006 | Hammersmark et al. |
| 6,383,171 | B1 | 5/2002 | Gifford et al. | 2006/0282149 A1 | 12/2006 | Kao |
| 6,419,693 | B1 | 7/2002 | Fariabi | 2006/0282150 A1 | 12/2006 | Olson et al. |
| 6,425,898 | B1 | 7/2002 | Wilson et al. | 2007/0027521 A1 | 2/2007 | Andreas et al. |
| 6,451,025 | B1 | 9/2002 | Jervis | 2007/0067012 A1 | 3/2007 | George et al. |
| 6,451,050 | B1 | 9/2002 | Rudakov et al. | 2007/0088368 A1 | 4/2007 | Acosta et al. |
| 6,468,298 | B1 | 10/2002 | Pelton | 2007/0088420 A1 | 4/2007 | Andreas et al. |
| 6,468,299 | B2 | 10/2002 | Stack et al. | 2007/0088422 A1 | 4/2007 | Chew et al. |
| 6,485,510 | B1 | 11/2002 | Camrud et al. | 2007/0100423 A1 | 5/2007 | Acosta et al. |
| 6,488,694 | B1 | 12/2002 | Lau et al. | 2007/0100424 A1 | 5/2007 | Chew et al. |
| 6,511,468 | B1 | 1/2003 | Cragg et al. | 2007/0106365 A1 | 5/2007 | Andreas et al. |
| 6,520,983 | B1 | 2/2003 | Colgan et al. | 2007/0118202 A1 | 5/2007 | Chermoni |
| 6,520,987 | B1 | 2/2003 | Plante | 2007/0118203 A1 | 5/2007 | Chermoni |
| 6,527,798 | B2 | 3/2003 | Ginsburg et al. | 2007/0118204 A1 | 5/2007 | Chermoni |
| 6,527,799 | B2 | 3/2003 | Shanley | 2007/0129733 A1 | 6/2007 | Will et al. |
| 6,529,549 | B1 | 3/2003 | Norrell et al. | | | |
| 6,555,157 | B1 | 4/2003 | Hossainy | FOREIGN PATENT DOCUMENTS | | |
| 6,575,993 | B1 | 6/2003 | Yock | EP | 274129 B1 | 5/1992 |
| 6,582,394 | B1 | 6/2003 | Reiss et al. | EP | 282143 B1 | 9/1993 |
| 6,605,062 | B1 | 8/2003 | Hurley et al. | EP | 533960 B1 | 10/1994 |
| 6,645,547 | B1 | 11/2003 | Shekalim et al. | EP | 0714640 | 5/1996 |
| 6,656,212 | B2 | 12/2003 | Ravenscroft et al. | EP | 0990426 A | 4/2000 |
| 6,666,883 | B1 | 12/2003 | Seguin et al. | WO | WO 86/03129 | 6/1986 |
| 6,679,909 | B2 | 1/2004 | McIntosh et al. | WO | WO 87/07510 | 12/1987 |
| 6,692,465 | B2 | 2/2004 | Kramer | WO | WO 88/09682 | 12/1988 |
| 6,702,843 | B1 | 3/2004 | Brown et al. | WO | WO 92/11890 | 7/1992 |
| 6,712,827 | B2 | 3/2004 | Ellis et al. | WO | WO 92/11895 | 7/1992 |
| 6,712,845 | B2 | 3/2004 | Hossainy | WO | WO 93/21985 | 11/1993 |
| 6,723,071 | B2 | 4/2004 | Gerdts et al. | WO | WO 94/11048 | 5/1994 |
| 6,743,251 | B1 | 6/2004 | Eder | WO | WO 94/11053 | 5/1994 |
| 7,137,993 | B2 | 11/2006 | Acosta et al. | WO | WO 95/03081 | 2/1995 |
| 7,147,655 | B2 | 12/2006 | Chermoni | WO | WO 95/03082 | 2/1995 |
| 7,147,656 | B2 | 12/2006 | Andreas et al. | WO | WO 95/11055 | 4/1995 |
| 7,175,653 | B2 | 2/2007 | Gaber | WO | WO 96/33677 | 10/1996 |
| 7,182,779 | B2 | 2/2007 | Acosta et al. | WO | WO 97/46174 | 12/1997 |
| 7,192,440 | B2 | 3/2007 | Andreas et al. | WO | WO 99/01087 | 1/1999 |
| 2001/0020181 A1 | | 9/2001 | Layne | WO | WO 00/15151 | 3/2000 |

| WO | WO 00/18302 | 4/2000 |
| WO | WO 00/32136 | 6/2000 |
| WO | WO 00/41649 | 7/2000 |
| WO | WO 01/91918 | 12/2001 |
| WO | WO 03/022178 | 3/2003 |
| WO | WO 03/051425 | 6/2003 |
| WO | WO 2004/017865 | 3/2004 |
| WO | WO 2004/043299 | 5/2004 |
| WO | WO 2004/043301 | 5/2004 |
| WO | WO 2004/043510 | 5/2004 |
| WO | WO 2004/052237 | 6/2004 |
| WO | WO 2006/130326 | 12/2006 |
| WO | WO 2006/135551 | 12/2006 |
| WO | WO 2007/053187 | 5/2007 |

OTHER PUBLICATIONS

Colombo, A., "The invatec bifurcation stent solution," *Bifurcation Stents: Novel Solutions*, Sep. 15-19, 2003, 24 pgs, Washington.

Cooley at al., "Applications of Ink-Jet Printing Technology to BioMEMs and Microfluidic Systems," *Proceedings, SPIE Conference on Microfluidics and BioMEMs*, Oct. 2001.

Hong, M. K. at al. "A New PTCA Balloon Catheter With Intramural Channels for Local Delivery of Drugs at Low Pressure," *Supplement to Circulation, Abstracts From the 65th Scientific Sessions*, 1992, vol. 88, No. 4, #1514.

Lefevre, T., at al, "Approach to coronary bifurcation stenting in 2003," *Euro PCR*, May 203, 28 pgs.

Stimpson et al, "Parallel Production of Oligonucleotide Arrays Using Membranes and Reagent Jet Printing," *BioTechniques*, Nov. 1998, 25:886-890.

U.S. Appl. No. 11/625,237, filed Jan. 19, 2007 in the name of Chermoni, Non-final Office Action mailed Mar. 16, 2010.

U.S. Appl. No. 12/503,756, filed Jul. 15, 2009 in the name of Chermoni, non-final Office Action mailed Nov. 22, 2010.

BALLOON CATHETER FOR MULTIPLE ADJUSTABLE STENT DEPLOYMENT

RELATED APPLICATION DATA

This application is a continuation of U.S. application Ser. No. 11/625,243 filed Jan. 19, 2007 which is a continuation of U.S. application Ser. No. 11/421,653 filed Jun. 1, 2006, now abandoned, which is a continuation of U.S. application Ser. No. 10/108,985 filed Mar. 29, 2002, now U.S. Pat. No. 7,147,655, which claims the benefit of foreign priority to IL 142332 filed Mar. 29, 2001, each of which application is hereby incorporated by reference in its entirety.

FIELD OF THE INVENTION

This invention relates to catheters and more specifically to such catheters that are used to implant a stent in an artery.

BACKGROUND OF THE INVENTION

Blood vessels, and particularly arteries, may become stenotic or occluded due to various atherosclerotic processes. A stenotic artery may be treated by balloon angioplasty in which an inflatable balloon mounted on a catheter tip is inserted into the arterial system and navigated through the arterial system to the diseased artery. The balloon is then inflated by means of a pressurized fluid. This causes the balloon to press radially on the arterial wall so as to open the stenosis. A stent may be crimped onto the balloon before insertion so that when the balloon is inflated the stent becomes expanded. The balloon is deflated and withdrawn leaving the expanded stent in the artery. These and other similar methods are well known to the skilled man of the art.

It is often necessary to treat several stenoses in a single angioplastic session. For example, it may be necessary to insert a large diameter stent at one location, a small diameter stent at a second location and to perform a balloon angioplasty without a stent at a third location. This could be accomplished by sequential insertion and withdrawal of a catheter, the catheter being loaded each time with the appropriate stent prior to insertion. This however would cause much discomfort to the patient, prolongs the duration of the procedure and increases the chances of damaging a blood vessel.

U.S. Pat. No. 6,027,519 discloses a catheter for deploying one or more stents. The stent has one or more individually expandable segments along its length. A stent, in its unexpanded state, is loaded onto each expandable segment of the catheter. The catheter is inserted into the vascular system and positioned with the first expandable segment in a stenosis. An axial force is then applied to the segment causing it to buckle outwards and expand the stent. The force is then removed causing the segment to unbuckle leaving the stent in its expanded state. The catheter is then navigated to another stenosis. This process is repeated until all of the stents have been deployed.

SUMMARY OF THE INVENTION

The present invention provides a catheter for deploying one or more stents in a cardiovascular system. The catheter is configured to carry one or more stents. Preferably, the catheter carries a plurality of stents. The stents may be of different or the same widths. An inflatable balloon is used to expand a stent surrounding the balloon. The catheter comprises a positioner for moving a stent relative to the balloon from a position in which the stent does not surround the balloon to a position that it does surround the balloon in order to prime the stent for expansion by the balloon. The phrase "for moving a stent relative to the balloon" includes two possibilities, i.e. moving the positioner relative to the balloon and moving the balloon relative to the positioner.

In one embodiment of the invention the positioner comprises an element configured to slide along the catheter and push the stents distally along the catheter so as to move a stent adjacent to the balloon into a position in which it surrounds the balloon. The sliding element is pushed along the catheter by means of a wire extending along the catheter from its proximal end to the sliding element. In this embodiment, the stents are deployed in the order in which they are carried by the catheter, starting with the stent closest to the balloon.

In another embodiment, the positioner comprises a flexible carriage configured to carry the one or more stents. The carriage is capable of sliding along the catheter in order to bring one of the stents from a position in which the stent does not surround the balloon to a position in which the stent surrounds the balloon. The carriage is moved in either direction along the catheter by means of a wire extending along the catheter from its proximal end to the carriage. It is also possible to position the stent opposite a desired location in the vascular system and slide the balloon through the carriage to a position opposite the stent. In this embodiment the stents may be deployed in the vascular system in any order.

It a third embodiment, the catheter comprises two positioners, one posterior positioner as described above in the first embodiment positioned posterior to the balloon, and a second anterior positioner positioned anterior to the balloon. In this embodiment, the anterior positioner may be distanced from the balloon so as to provide a storage space between the anterior positioner and the balloon. The balloon in this embodiment may be a conventional balloon used in balloon angioplasty. In this embodiment also, the stents may be deployed in the vascular system in any order, and may be of different lengths.

In use, the catheter is loaded with one or more stents and inserted into a vascular system. The catheter is navigated through the vascular system until the balloon or stent is positioned at a first desired location, typically the site of a stenosis. The stent or balloon is then moved by the positioner so that the stent surrounds the balloon and the balloon is inflated so as to expand the stent. The balloon is then deflated, leaving the expanded stent at the first desired location. This process may be repeated, each time deploying a different stent at a different location. After one or more of the stents have been deployed, the catheter may be removed from the vascular system.

The invention also provides a method for deploying a stent in a desired location of a vascular system comprising the steps of:

(a) inserting a catheter according to the invention carrying one or more stents into the vascular system, (b) navigating the catheter through the vascular system until the balloon is positioned in the desired location;

(c) moving a stent from a first position in which it does not surround the balloon to a second position in which it surrounds the balloon;

(d) inflating the balloon so as to expand the stent; and (e) deflating the balloon.

BRIEF DESCRIPTION OF THE DRAWINGS

In order to understand the invention and to see how it may be carried out in practice, a preferred embodiment will now be described, by way of non-limiting examples only, with reference to the accompanying drawings, in which.

DETAILED DESCRIPTION OF THE INVENTION

Example I

Figure 1:
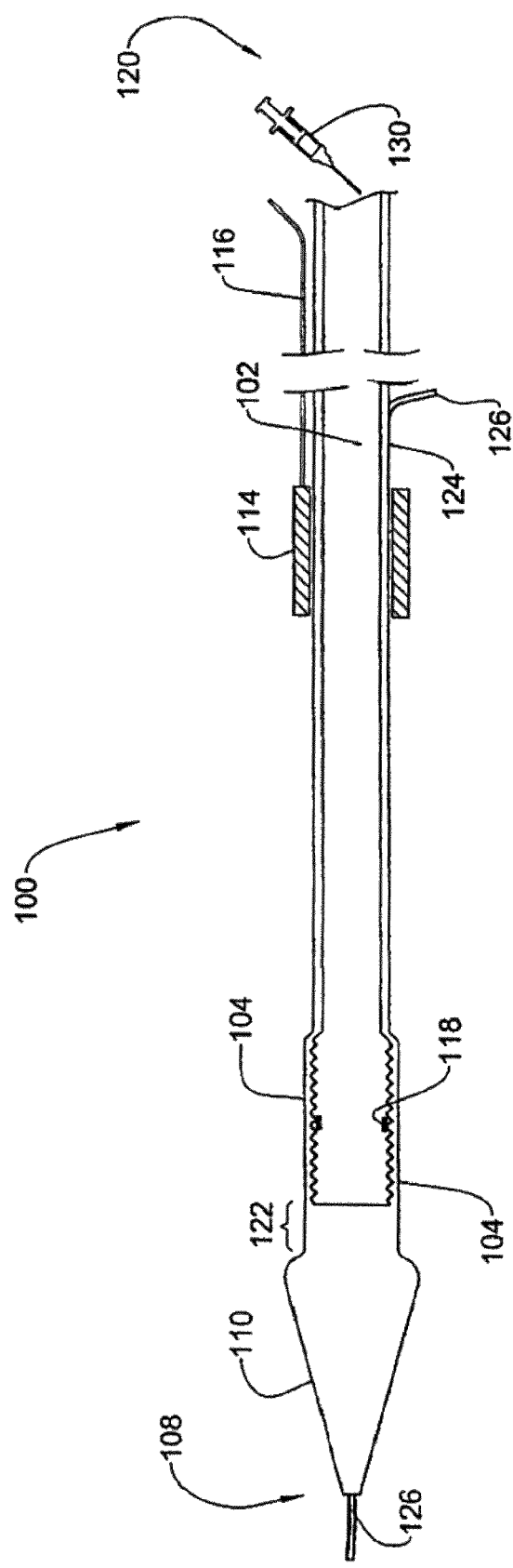
FIG. 1 shows a catheter in accordance with one embodiment of the invention.

FIG. 1 shows a catheter 100 for deploying stents in accordance with one embodiment of the invention. The catheter 100 has a distal end 108 and a proximal end 120. The catheter 100 comprises a flexible tube 102, which is connected to an inflatable balloon 104 proximate to its distal end. The balloon 104 is shown in the Figure in its deflated state. A radio-opaque marker 118 is located on the balloon wall. The catheter 100 has at its distal end 108 a tapered tip 110 that may be inserted into a stenosis in order to open the stenosis. A syringe 130 may be used to introduce a fluid into the tube 102 in order to inflate the balloon 104 as described in detail below.

A longitudinal shaft 124 in the wall of the tube 102 is configured to receive a guidewire 126 used in navigating the catheter in the vascular system. A neck region 122 of the tube 102 intervenes between the distal end of the balloon 104 and the tip 110. The proximal end of the tip 110 is broadened to form a shoulder at the distal end of the neck region 122. A sliding positioner element in the form of an annular sliding ring 114 is mounted on the tube 102 proximal to the balloon 104. The ring 114 is slidable along the tube 102 by means of a wire 116 that extends along the length of the tube 102 from the proximal end 120 of the catheter to the ring 114.

The sliding ring 114 and the wire 116 form a positioner for moving a stent from a position which it does not surround the balloon 104 to a position in which it surrounds the balloon 104.

Figure 2:
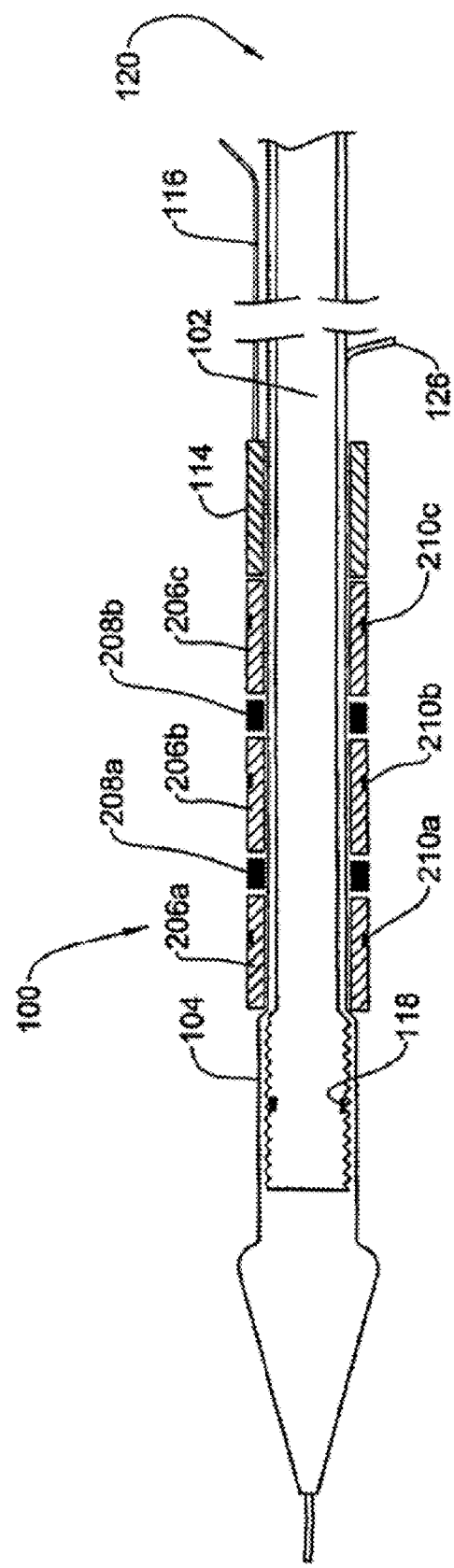
FIG. 2 shows the catheter of FIG. 1 carrying stents.

FIG. 2 shows the catheter 100 having a plurality of stents (three are shown in FIG. 2) 206a, 206b and 206c, mounted on the tube 102 between the sliding ring 114 and the balloon 104. The stents are separated from each other by separating rings 208a and 208b. The sliding ring 114 has been positioned so that the separating rings 208a and 208b and the stent 206 are contiguous with the balloon 104. Each stent 206 bears a radio-opaque annular markers 210a, 210b and 210c.

Figure 3:
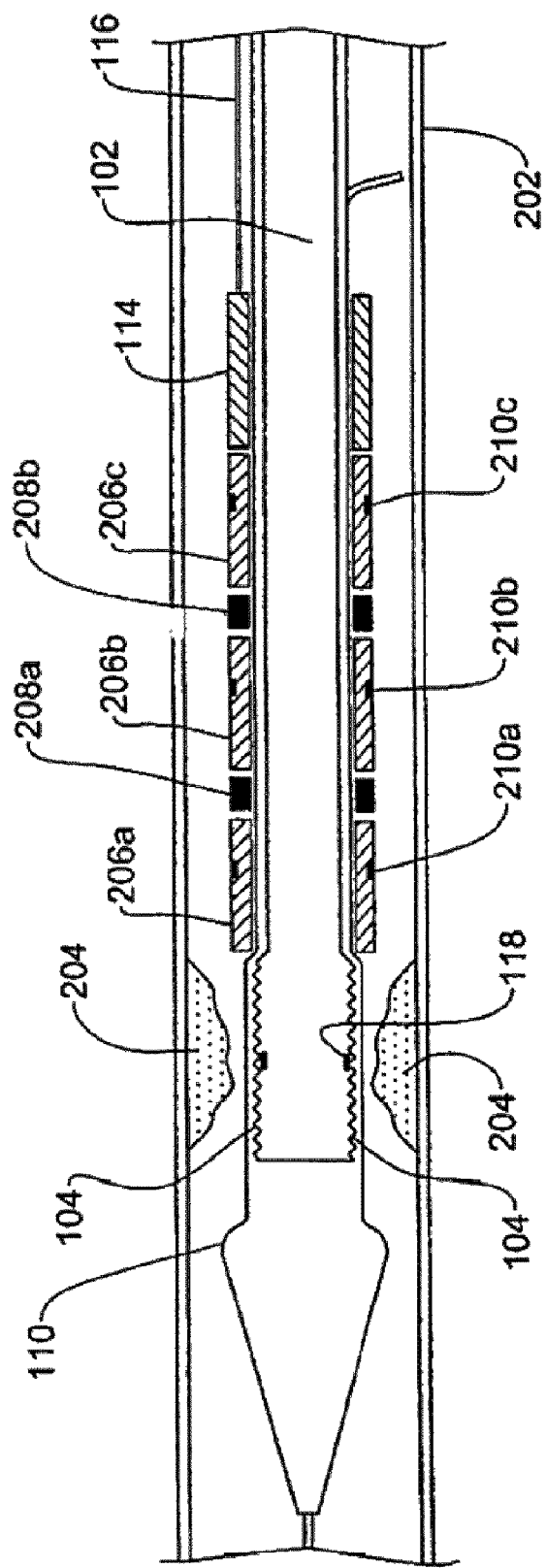
FIG. 3 shows the catheter at FIG. 1 inserted in a blood vessel.
Figure 4:
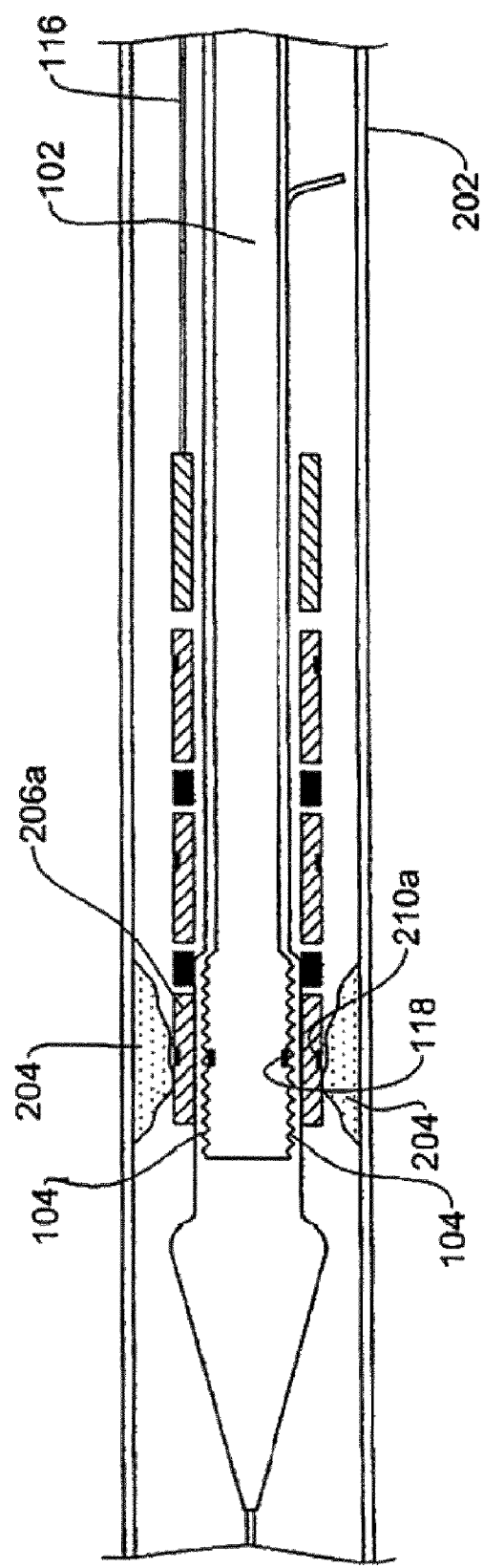
FIG. 4 shows the catheter of FIG. 1 with a stent surrounding a balloon on the catheter.

In use, the catheter 100 is introduced into the vascular system and navigated to a stenosis by methods well known in the art. FIG. 3 shows the catheter 100 after having been navigated through the vascular system and positioned inside a blood vessel 202. The balloon is located opposite a stenotic region 204 of the blood vessel 202. The wire 116 is used to slide the sliding ring 114 distally along the tube 102 so as to push the stents 206a, 206b, 206c, distally. The sliding ring 114 is pushed distally along the tube 102 so that the stent 206a is pushed over and around the balloon 104, which is thereby brought into the lumen of the stent 206a, and the marker 118 on the balloon coincides with the marker 210a of the stent, as determined for example by x-ray angiography. FIG. 4 shows the stent 206a surrounding the balloon 104.

Figure 5:
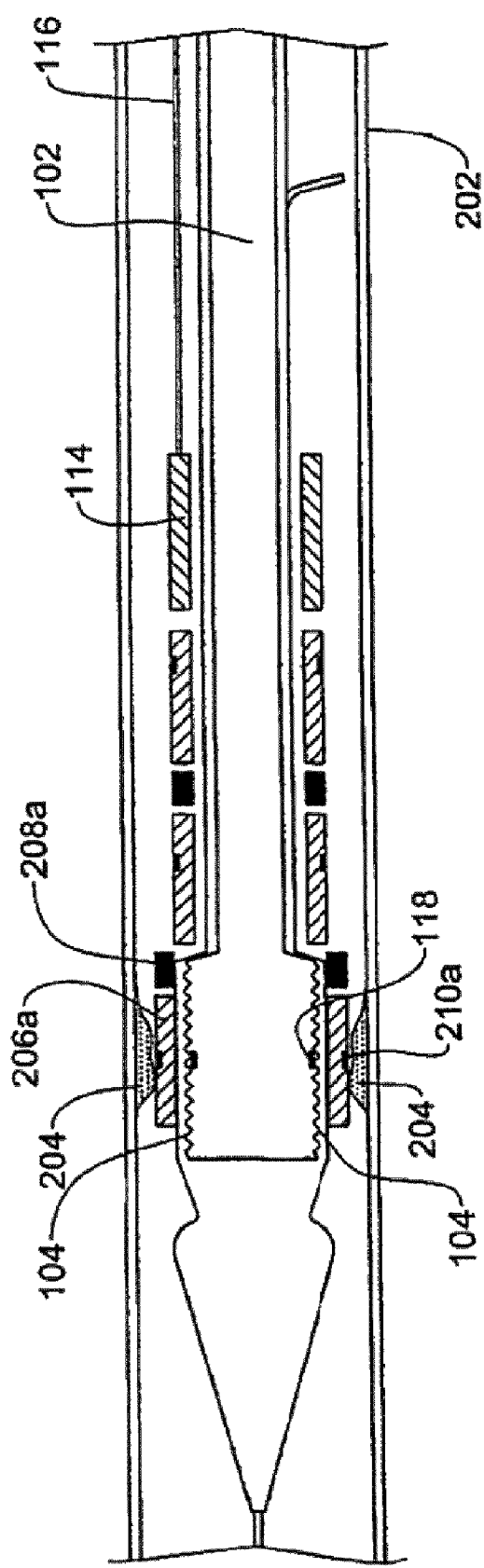
FIG. 5 shows the catheter in FIG. 1 after inflation of the balloon.

A fluid is then introduced into the tube 102. The fluid passes through the tube 102 and inflates the balloon 104. It will be understood that the balloon may be inflated by other conventional means, as are known in the art. Inflation of the balloon 104 expands the stent 206a onto the stenotic region of the blood vessel 202, as shown in FIG. 5.

The fluid is then withdrawn from the tube 102. Withdrawal of the fluid from the tube 102 causes the balloon to deflate. After deflation of the balloon, the stent 206a remains in situ in its expanded state.

The catheter may then be navigated through the arterial system until the catheter is positioned with the balloon 104 at another stenotic region of a blood vessel. The sliding ring is pushed distally by the wire 116 so that the succeeding stent 206b overlies the balloon 104 and the marker 118 coincides with the marker 210b on the stent 206b. The distal separating ring 208a is pushed along the tube 102, beyond the balloon 104 to the neck region 122 of the tube, where the separating rings are stored. The shoulder of the tip 110 retains the separating rings on the neck region. This process may be repeated until some or all of the stents 206 have been deployed. The catheter is then removed from the body.

Example II

Figure 6:
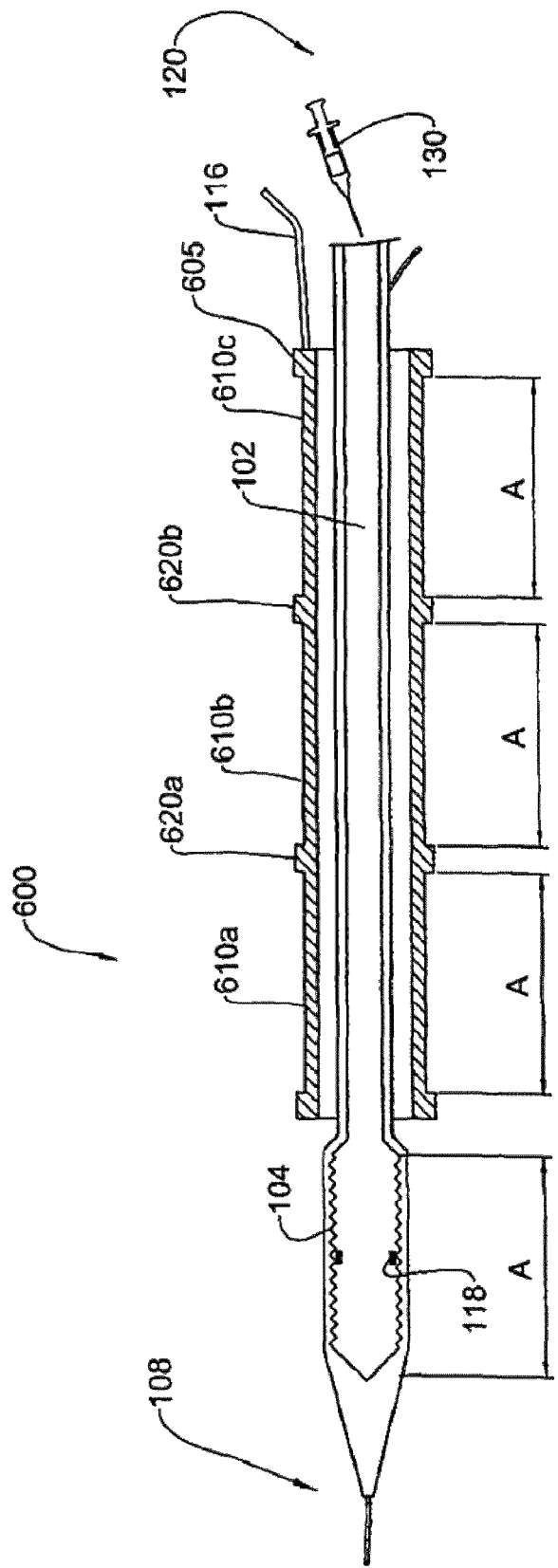
FIG. 6 shows a catheter in accordance with another embodiment of the invention.

FIG. 6 shows a catheter 600 for deploying stents in accordance with another embodiment of the invention. The embodiment of FIG. 6 has many components in common with the embodiment of FIG. 1, and similar components are identified by the same reference numeral in both embodiments.

The embodiment of FIG. 6 has a cylindrical carriage 605 mounted on the tube 102. The carriage has a plurality of annular depressions (three are shown in FIG. 6) 610a, 610b and 610c configured to receive a stent as described below. The depressions 610 all have the same length A as indicated in FIG. 6, which is essentially equal to the length of the balloon 104. Between the depressions 610 are barriers 620a and 620b. The carriage 605 is made from an elastic material such as rubber. The carriage 605 is slidable along the tube 102 by means of a wire 116 that extends along the length of the tube 102 from the proximal end 120 of the catheter to the carriage 605. The carriage 605 and the wire 116 form a positioner for moving a stent from a position in which it does not surround the balloon 104 to a position in which it surrounds the balloon 104.

Figure 7:
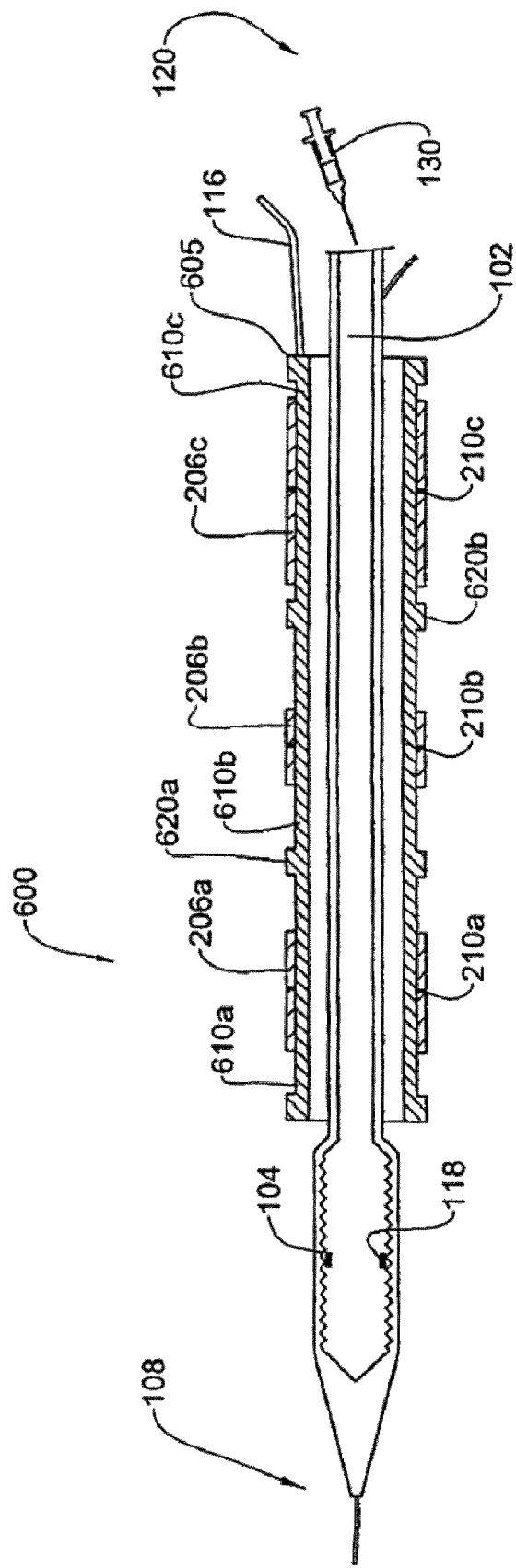
FIG. 7 shows the catheter of FIG. 6 carrying stents.

FIG. 7 shows the catheter 600 having a plurality of stents (three are shown in FIG. 7) 206a, 206b and 206c mounted on the annular depressions of the tube 102. The stents are separated from each other by the barriers 620a and 620b. In the present embodiment the stents are of different lengths. However, they may also be of the same length. Each stent 206 bears a radio-opaque annular marker 210a, 210b and 210c.

Figure 8:
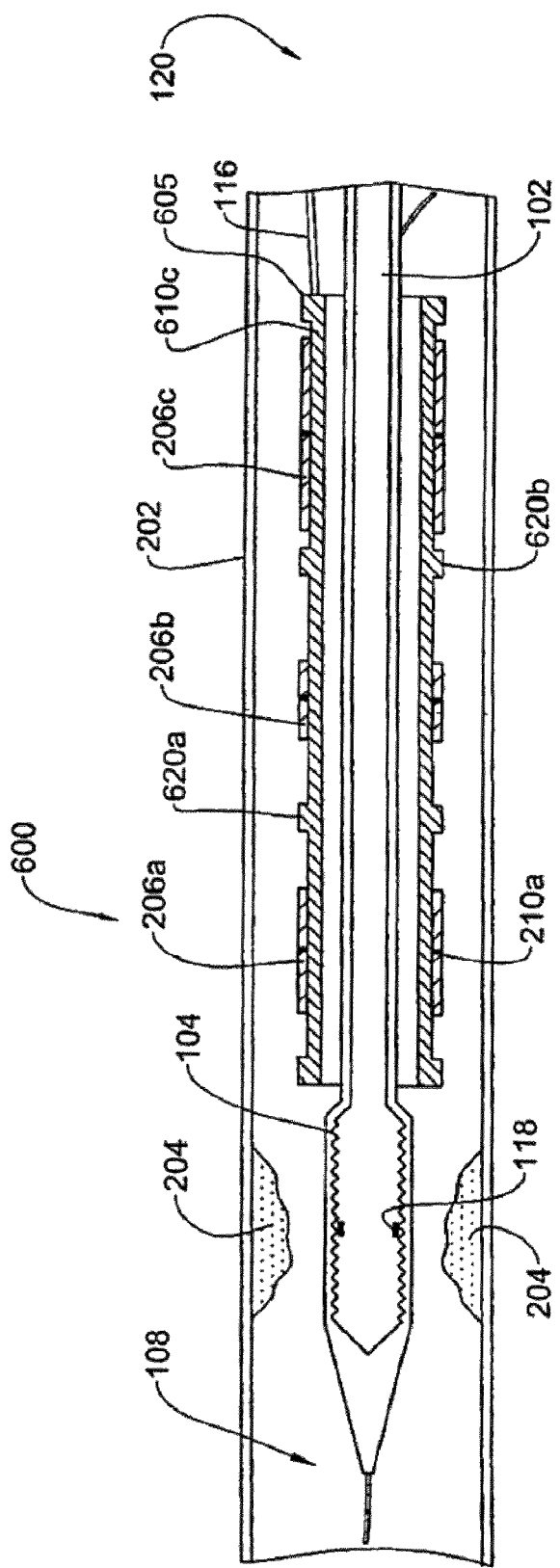
FIG. 8 shows the catheter at FIG. 6 inserted in a blood vessel.
Figure 9:
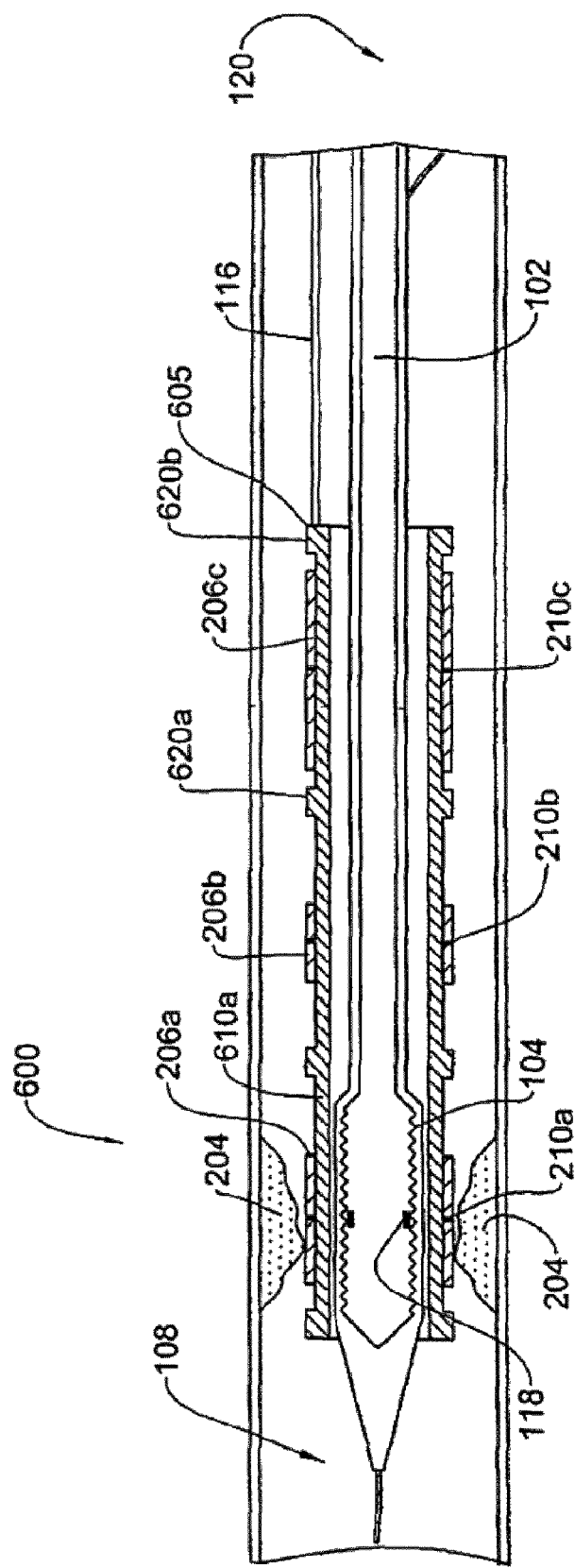
FIG. 9 shows the catheter of FIG. 6 with a stent surrounding a balloon on the catheter.

The catheter 600 is introduced into the vascular system and navigated to a stenosis by methods well known in the art. FIG. 8 shows the catheter 600 after having been navigated through the vascular system and positioned inside a blood vessel 202. The balloon is located within a stenotic region 204 of the blood vessel 202. The wire 116 is used to slide the cage 605 distally along the tube 102 so as to move the stents 206 distally. The carriage 605 is pushed distally along the tube 102 until the balloon 104 is brought into the lumen of the stent 206a and the marker 118 on the tube coincides with the marker 210a, as determined for example by x-ray angiography. In a similar manner, the balloon may be slid within the carriage until it is positioned opposite the stent. FIG. 9 shows the stent 206a surrounding the balloon 104.

Figure 10:
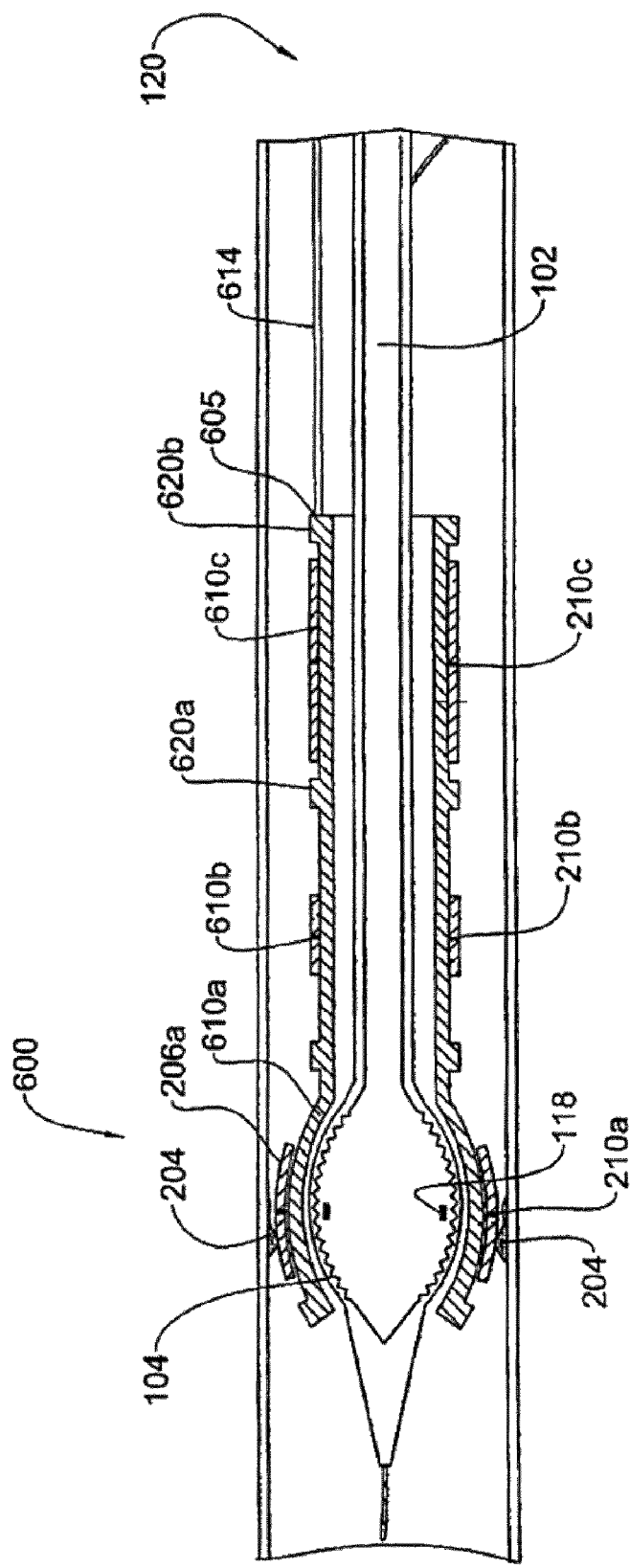
FIG. 10 shows the catheter in FIG. 6 after inflation of the balloon.

A fluid is then introduced into the tube 102. The fluid passes through the tube 102 and inflates the balloon 104. Inflation of the tube 104 expands the portion of the carriage 605 surrounding the balloon 104 which in turn expands the stent 206a onto the stenotic region of the blood vessel 202, as shown in FIG. 10.

The fluid is then withdrawn from the tube 102 into the syringe 130. Withdrawal of the fluid from the tube 102 causes the balloon to deflate. After deflation of the balloon, the stent 206a remains in its expanded state.

The catheter is then navigated through the arterial system until the catheter is positioned with the balloon 104 in another stenotic region of a blood vessel. The catheter is then pushed distally by the wire 116 so that the stent 206b overlies the balloon 104 and the marker 118 coincides with the marker 210b on the stent 206b. In this embodiment, the stents may be deployed in any order. This process may be repeated until some or all of the stents 206 have been deployed. The catheter is then removed from the body.

Example III

Figure 11:
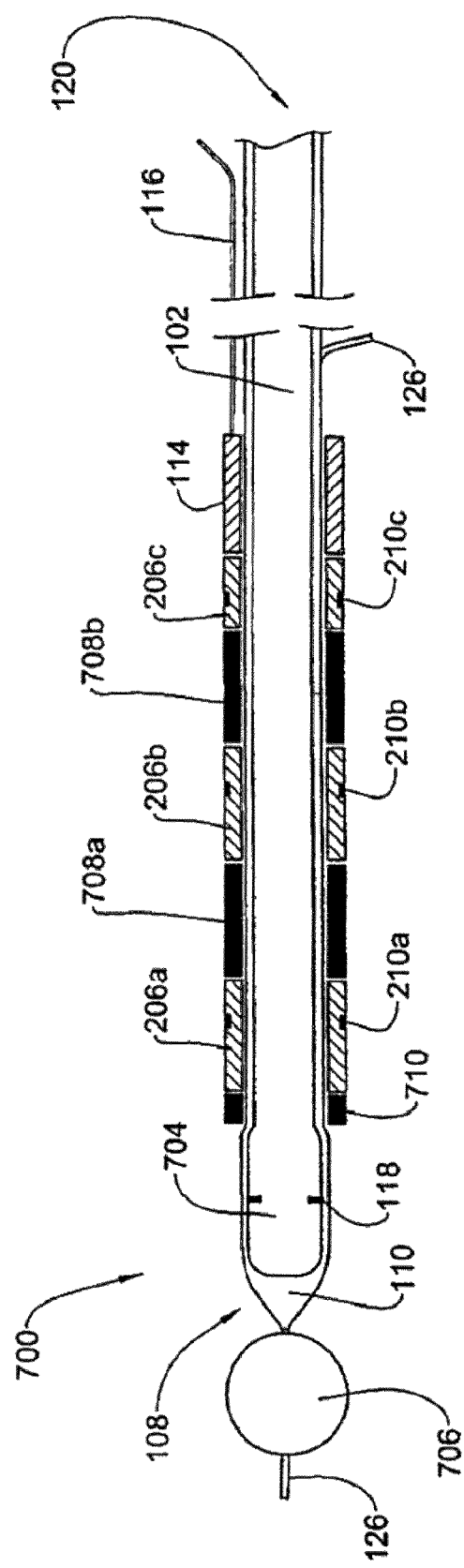
FIG. 11 is a sectional side view of a catheter in accordance with another embodiment of the invention.

This example illustrates an embodiment which is an improvement over the embodiment described in Example I. With reference to FIG. 11, there is shown a catheter 700 having a distal end 108 and a proximal end 120. As in FIG. 1, the catheter 700 comprises a flexible tube 102, which is connected to an inflatable balloon 704 proximate to its distal end. A radio-opaque marker 118 is located on the balloon wall. The catheter 700 has at its distal end 108 a tapered tip 110, but unlike in Example I, there is no neck region, and the tip is not enlarged. The balloon in this embodiment may be a conventional inflatable balloon used in balloon angioplasty.

As in Example I, a guidewire 126 extends along the tube 102, exiting at the distal end 108 of the catheter. An anterior positioner in the form of a perforated sphere 706 is fixed to the guidewire anterior to the balloon 704, e.g. the guidewire passes through a bore channel extending through the sphere. The diameter of the sphere is slightly larger than the diameter of the retracted stents which are mounted on the catheter. The purpose of the sphere will be explained below.

The catheter 700 has a sliding ring 114 (being the posterior positioner) and a plurality of stents (three are shown in FIG. 11) 206a, 206b and 206c, mounted on the tube 102 between the sliding ring 114 and the balloon 704. While the anterior stents are generally of the same length, the posterior stent may be longer or shorter. In the illustrated embodiment, the posterior stent 206c is shorter than the other stents. Each stent 206 bears at least one radio-opaque marker 210a, 210b and 210c, respectively. The stents are separated by separating rings 708a and 708b which are of the same length as the anterior stents. An anterior ring 710 is positioned between the most anterior stent 206a and the balloon 704 and protects the distal edge of the anterior stent. This anterior ring may be shorter than the separating rings.

Figure 12:
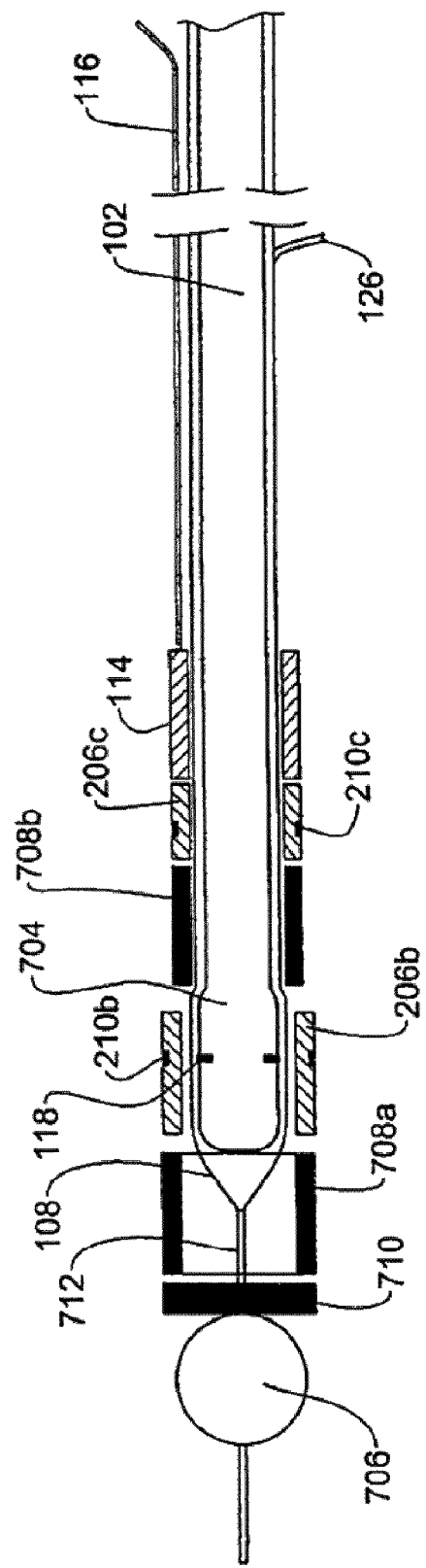
FIG. 12 illustrates the operation of the embodiment illustrated in FIG. 11.

The operation of this embodiment may be understood with reference to FIG. 12. As in Example I, the wire 116 is used to slide the sliding ring 114 distally along the tube 102 so as to push the stents 206a, 206b, 206c, distally. The sphere 706 is distanced from the distal end 108 of the catheter by pushing the guidewire 126, thus providing free guidewire 712 on which components of the catheter may be stored. In FIG. 12, it may be seen that the anterior ring 710 and the separating ring 708a have been pushed beyond the balloon 704 and onto the free guidewire 712. The anterior stent 206a (not shown) has been expanded and deployed within the blood vessel wall, and the middle stent 206b is mounted on the balloon 704, ready to be expanded. The radio-opaque marker 210b of the stent 206b is positioned opposite the radio-opaque marker 118 of the balloon 704.

Thus, this embodiment also differs from that of Example I in having more room to store the separating rings. In addition, all of the mounted stents and rings may be moved distally and proximally by pulling and pushing the anterior and posterior positioners, being the sphere 706 and sliding ring 114, respectively, so that the stents may be deployed in any order. This differs from Example I where the stents were required to be deployed in the order in which they were placed on the catheter.

Figure 13:
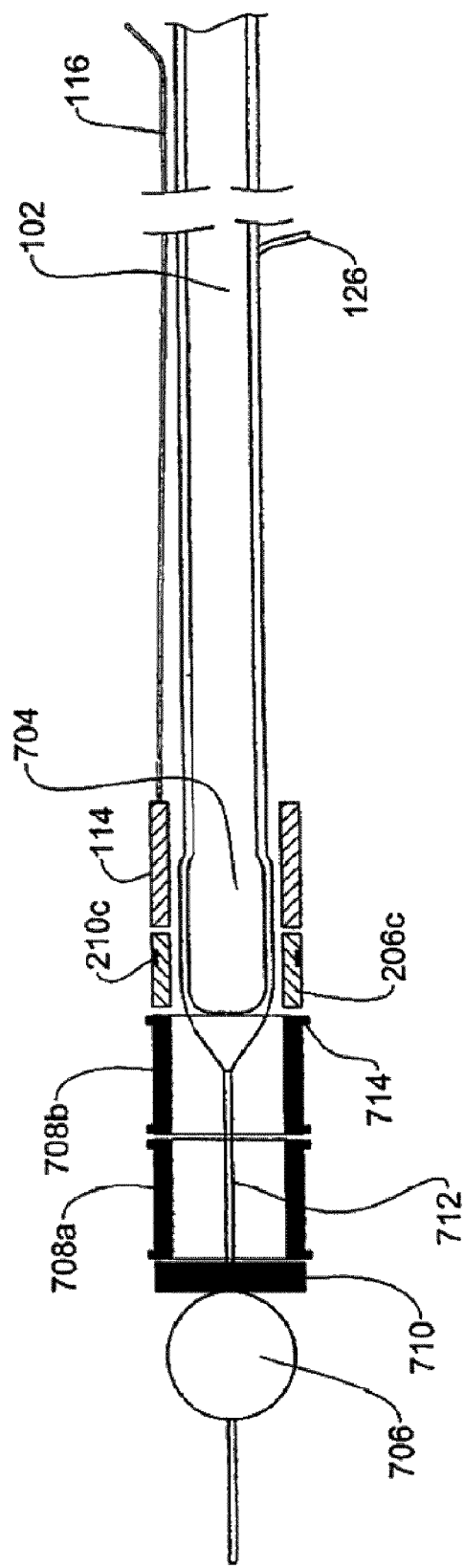
FIG. 13 illustrates another detail of the operation of the embodiment of FIG. 11.

FIG. 13 shows the catheter after the 2 anterior stents 206a and 206b (not shown) have been deployed, and the anterior 710 and separating 708a & 708b rings are positioned on the free guidewire 712 between the sphere 706 and the balloon 704. It may be seen that the separating rings have annular protrusions 714 protruding from their outer surface. The purpose of these protrusions is to protect the blood vessel inner wall from being injured by the stents as the catheter travels through the vessel. The posterior stent 206c is mounted on the distal half of the balloon 704, while the anterior portion of the sliding ring 114 envelops the proximal end of the balloon. Thus, when the balloon is inflated, only the distal half expands (since the sliding ring resists the pressure of the balloon), expanding the stent 206c and deploying it in the blood vessel.

What is claimed is:

1. A method of delivering a plurality of stents, comprising:
    intravascularly positioning a catheter proximate or adjacent to a first lesion, the catheter having a distal end, an inflatable balloon near the distal end, at least a first stent and a second stent slidably positionable into direct contact upon the balloon via a positioner which is slidable longitudinally along the catheter independently of each of the stents, and a separating mechanism comprising a separating ring positioned between the first stent and the second stent, wherein the at least first and second stents can be arranged in any order along the catheter;
    positioning the first stent such that the first stent is positioned into direct contact upon the balloon, whereby the first stent to be expanded is further separated from the second stent;
    expanding the balloon to expand the first stent at the first lesion while the second stent is retained unexpanded on the catheter;
    repositioning the catheter proximate or adjacent to a second lesion; and
    expanding the balloon to expand the second stent at the second lesion,
    wherein the first stent and the second stent have different lengths.

2. The method of claim 1 wherein prior to expanding the balloon to expand the first stent comprises slidably adjusting the positioner over the balloon to constrain a portion of the balloon from expanding such that a length of the expanded balloon is coextensive with a length of the first stent.

3. The method of claim 1 wherein the separating mechanism is movable relative to the balloon.

4. The method of claim 1 wherein positioning the first stent further comprises slidably urging a sliding element of the positioner along the catheter to push at least the first and second stents distally along the catheter so as to move the first stent adjacent to the balloon into a position in which it surrounds the balloon.

5. The method of claim 4 wherein urging the sliding element comprises urging a proximal end of a wire attached to the sliding element and extending longitudinally along a length of the catheter such that the sliding element slides along the catheter in response to a longitudinal movement of the wire.

6. The method of claim 1 wherein the second lesion is at a location separate from the first lesion.

7. The method of claim 1 wherein prior to expanding the balloon to expand the second stent, adjusting an expandable portion of the balloon such that the balloon expands along a length which is coextensive with a length of the second stent.

8. The method of claim 1 wherein prior to expanding the balloon to expand the second stent, slidably adjusting the positioner over the balloon to constrain a portion of the balloon from expanding.

9. The method of claim 1 wherein expanding the balloon to expand the second stent comprises expanding the balloon within the second stent such that a length of the expanded balloon is coextensive with a length of the second stent.

10. A method of delivering a plurality of stents, comprising:
intravascularly positioning a catheter proximate or adjacent to a first lesion, the catheter having a distal end, an inflatable balloon near the distal end, a first stent, a second stent adjacent to and proximal to the first stent, the first stent and the second stent each slidably positionable to surround the balloon via a positioner which is slidable longitudinally along the catheter independently of each of the stents, and a separating mechanism comprising a separating ring positioned between the first and the second stent;
sliding the first stent via the positioner into direct contact upon the balloon;
separating the first stent from the second stent such that while the first stent is in direct contact with the balloon the second stent is proximal to the balloon;
expanding the balloon to expand the first stent at the first lesion;
sliding the second stent via the positioner toward the distal end so that the second stent is positioned in direct contact upon the balloon;
repositioning the catheter proximate or adjacent to a second lesion; and
expanding the balloon to expand the second stent at the second lesion.

11. The method of claim 10 wherein sliding the first stent comprises directly surrounding the balloon with the first stent such that the first stent overlays the balloon without an intervening member.

12. The method of claim 10 wherein the separating mechanism is movable relative to the balloon.

13. The method of claim 10 wherein sliding the second stent comprises urging a sliding element of the positioner along the catheter to push at least the second stent distally along the catheter so as to move the second stent adjacent to the balloon into a position in which it surrounds the balloon.

14. The method of claim 13 wherein urging the sliding element comprises urging a proximal end of a wire attached to the sliding element and extending longitudinally along a length of the catheter such that the sliding element slides along the catheter in response to a longitudinal movement of the wire.

15. The method of claim 10 wherein repositioning the catheter comprises repositioning the second stent proximate or adjacent to the second lesion at a location separate from the first lesion.

16. The method of claim 10 wherein prior to expanding the balloon to expand the second stent, adjusting an expandable portion of the balloon such that the balloon expands along a length which is coextensive with a length of the second stent.

17. The method of claim 10 wherein prior to expanding the balloon to expand the second stent, slidably adjusting the positioner over the balloon to constrain a portion of the balloon from expanding.

18. The method of claim 10 wherein expanding the balloon to expand the second stent comprises expanding the balloon within the second stent such that a length of the expanded balloon is coextensive with a length of the second stent.

19. A method of delivering a plurality of stents, comprising:
intravascularly advancing a catheter proximate or adjacent to a first lesion, the catheter carrying a plurality of stents slidably positionable in direct contact upon an inflatable balloon near a distal end of the catheter via a positioner which is slidable longitudinally along the catheter independently of each of the stents, the catheter further carrying a separating mechanism comprising separating rings positioned between adjacent stents;
separating at least one stent from a remainder of the plurality of stents by sliding the positioner to place the one stent in direct contact with the balloon;
expanding the one stent at the first lesion while the remainder of stents is retained unexpanded on the catheter; and
removing the catheter with the remainder of stents from the first lesion;
wherein the one stent has a deployed length when expanded greater than the length of one of the remainder of stents retained on the catheter.

20. The method of claim 19 further comprising selecting a second stent for expansion from the remainder of stents, sliding the second stent upon the balloon, and slidably adjusting the positioner over the balloon to constrain a portion of the balloon from expanding such that a length of the expanded balloon is coextensive with a length of the second stent.

21. The method of claim 20 further comprising expanding the balloon to expand the second stent such that a length of the expanded balloon is coextensive with a length of the second stent.

22. The method of claim 19 wherein the separating mechanism is movable relative to the balloon.

23. The method of claim 19 wherein sliding the one stent comprises urging a sliding element of the positioner along the catheter to push at least the one stent distally along the catheter so as to move the one stent adjacent to the balloon into a position in which it surrounds the balloon.

24. The method of claim 23 wherein urging the sliding element comprises urging a proximal end of a wire attached to the sliding element and extending longitudinally along a length of the catheter such that the sliding element slides along the catheter in response to a longitudinal movement of the wire.

25. A method of delivering a plurality of stents, comprising: positioning a catheter in a vessel having a first lesion and a second lesion, the catheter having a shaft, a distal tip, a plurality of stents over the shaft proximal to the distal tip and slidably positionable in direct contact upon an inflatable balloon near a distal end of the catheter via a positioner which is slidable longitudinally along the catheter independently of each of the stents, and a separating mechanism comprising separating rings positioned between adjacent stents, wherein the plurality of stents can be arranged in any order along the catheter;

advancing the catheter so that the distal tip is distal to the first lesion;

separating one stent from the plurality of stents such that the one stent is positioned upon the balloon;

expanding the one stent at the first lesion while at least a second stent of the plurality of stents is retained unexpanded on the catheter, the distal tip being maintained in a stationary position distal to the first lesion while the at least one stent is expanded;

repositioning the catheter so that the distal tip is distal to a second lesion spaced apart from the first lesion; and expanding the second stent at the second lesion, the distal tip being maintained in a stationary position distal to the second lesion while the second stent is expanded.

26. The method of claim 25 wherein expanding the one stent comprises inflating a balloon to reconfigure the at least one stent from a low-profile configuration to an expanded configuration for placement against the first lesion.

27. The method of claim 25 wherein prior to expanding the one stent, slidably adjusting the positioner over the balloon to constrain a portion of the balloon from expanding such that a length of the expanded balloon is coextensive with a length of the one stent.

28. The method of claim 25 wherein the separating mechanism is movable relative to the balloon.

29. The method of claim 25 wherein repositioning the catheter comprises repositioning the second stent proximate or adjacent to the second lesion at a location separate from the first lesion.

30. The method of claim 25 wherein expanding the second stent comprises inflating the balloon to reconfigure the second stent from a low-profile configuration to an expanded configuration for placement against the second lesion.

31. The method of claim 25 wherein expanding the second stent comprises expanding the balloon within the second stent such that a length of the expanded balloon is coextensive with a length of the second stent.

\* \* \* \* \*